US012778870B2

(12) United States Patent
Schwartz et al.

(10) Patent No.: US 12,778,870 B2
(45) Date of Patent: Nov. 3, 2026

(54) SYNERGISTIC ANTIOXIDANT COMPOSITIONS

(71) Applicant: The Procter & Gamble Company, Cincinnati, OH (US)

(72) Inventors: James Schwartz, Cincinnati, OH (US); Leo Timothy Laughlin, II, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 419 days.

(21) Appl. No.: 18/330,750

(22) Filed: Jun. 7, 2023

(65) Prior Publication Data

US 2024/0407990 A1 Dec. 12, 2024

(51) Int. Cl.

| | |
|---|---|
| ***A61K 8/49*** | (2006.01) |
| ***A61K 8/42*** | (2006.01) |
| ***A61K 8/67*** | (2006.01) |
| ***A61Q 5/02*** | (2006.01) |
| ***A61Q 5/12*** | (2006.01) |

(52) U.S. Cl.

CPC .............. *A61K 8/4926* (2013.01); *A61K 8/42* (2013.01); *A61K 8/675* (2013.01); *A61Q 5/02* (2013.01); *A61K 2800/522* (2013.01)

(58) Field of Classification Search

CPC ........ A61K 8/4926; A61K 8/42; A61K 8/675; A61K 2800/522; A61Q 5/02; A61Q 5/12

See application file for complete search history.

(56) References Cited

U.S. PATENT DOCUMENTS

| | | | |
|---|---|---|---|
| 4,796,812 | A | 1/1989 | Grollier |
| 4,885,107 | A | 12/1989 | Wetzel |
| 5,624,666 | A | 4/1997 | Coffindaffer et al. |
| 5,675,013 | A | 10/1997 | Haní et al. |
| 6,060,044 | A | 5/2000 | Cretois |
| 8,360,973 | B2 | 1/2013 | Bazin |
| 9,034,792 | B2 | 5/2015 | Stark et al. |
| 9,126,163 | B2 | 9/2015 | Giessler-blank et al. |
| 9,996,674 | B2 | 6/2018 | Segman |
| 10,227,551 | B2 | 3/2019 | Arhancet et al. |
| 10,543,157 | B2 | 1/2020 | Davis |
| 10,925,823 | B2 | 2/2021 | Schwartz |
| 11,433,015 | B2 | 9/2022 | Oh et al. |
| 11,433,070 | B2 | 9/2022 | Richards et al. |
| 11,701,316 | B2 | 7/2023 | Richards et al. |

(Continued)

FOREIGN PATENT DOCUMENTS

| | | | |
|---|---|---|---|
| CN | 200957387 | Y | 10/2007 |
| CN | 101647430 | A | 2/2010 |

(Continued)

OTHER PUBLICATIONS

PCT Search Report and Written Opinion for PCT/US2024/032769 dated Oct. 28, 2024, 13 pages.

(Continued)

*Primary Examiner* — Monica A Shin
*Assistant Examiner* — Dongxiu Zhang
(74) *Attorney, Agent, or Firm* — Linda M. Sivik

(57) ABSTRACT

The present invention is directed to a personal care composition comprising a hydroxy pyridone; niacinamide; and panthenol; wherein when the hydroxy pyridone is at about 0.8%, there is a synergistic antioxidant activity when niacinamide is from about 0.005% to about 0.1% and panthenol is from about 0.005% to about 0.2%.

4 Claims, 2 Drawing Sheets

(56) References Cited

U.S. PATENT DOCUMENTS

| | | | |
|---|---|---|---|
| 11,980,612 | B2 | 5/2024 | Richards |
| 11,980,679 | B2 | 5/2024 | Renock |
| 2002/0150287 | A1 | 10/2002 | Kobayashi |
| 2002/0183988 | A1 | 12/2002 | Skaanning |
| 2003/0215522 | A1 | 11/2003 | Johnson |
| 2004/0018165 | A1 | 1/2004 | Konig |
| 2004/0213751 | A1 | 10/2004 | Schwartz |
| 2007/0092547 | A1 | 4/2007 | Birnbaum |
| 2008/0220103 | A1 | 9/2008 | Bimbaum et al. |
| 2009/0155383 | A1 | 6/2009 | Kitko et al. |
| 2009/0222956 | A1 | 9/2009 | Cush et al. |
| 2009/0274642 | A1 | 11/2009 | Dawson, Jr. et al. |
| 2010/0106679 | A1 | 4/2010 | Yamaguchi |
| 2010/0234366 | A1 | 9/2010 | Van Ravenzwaay et al. |
| 2011/0055978 | A1 | 3/2011 | Jamet et al. |
| 2011/0190129 | A1 | 8/2011 | Bell et al. |
| 2011/0195846 | A1 | 8/2011 | Troppmann et al. |
| 2011/0217340 | A1 | 9/2011 | Angus et al. |
| 2012/0022021 | A1 | 1/2012 | Rademacher et al. |
| 2012/0065126 | A1 | 3/2012 | Brueser et al. |
| 2012/0309733 | A1 | 12/2012 | Chang et al. |
| 2013/0064900 | A1 | 3/2013 | Herring |
| 2013/0196852 | A1 | 8/2013 | Rannard et al. |
| 2013/0197275 | A1 | 8/2013 | Spiegler et al. |
| 2014/0028822 | A1 | 1/2014 | Khadavi |
| 2014/0071456 | A1 | 3/2014 | Podoleanu et al. |
| 2014/0120048 | A1 | 5/2014 | Krueger |
| 2014/0171471 | A1 | 6/2014 | Krueger |
| 2014/0271930 | A1 | 9/2014 | Kerr et al. |
| 2014/0273055 | A1 | 9/2014 | Kerr et al. |
| 2014/0378810 | A1 | 12/2014 | Davis |
| 2015/0010487 | A1 | 1/2015 | Snyder et al. |
| 2015/0217465 | A1 | 8/2015 | Krenik |
| 2015/0272865 | A1 | 10/2015 | Mette |
| 2015/0313819 | A1 | 11/2015 | Edelson |
| 2016/0038397 | A1 | 2/2016 | Markland |
| 2016/0310393 | A1 | 10/2016 | Chang |
| 2016/0346184 | A1 | 12/2016 | Schwartz et al. |
| 2017/0135932 | A1 | 5/2017 | Schwartz et al. |
| 2017/0225006 | A1 | 8/2017 | Anderson |
| 2017/0270593 | A1 | 9/2017 | Sherman |
| 2017/0304172 | A1 | 10/2017 | Chang et al. |
| 2017/0367963 | A1 | 12/2017 | Kadir |
| 2018/0040052 | A1 | 2/2018 | Robinson |
| 2018/0225673 | A1 | 8/2018 | Dubey |
| 2018/0311135 | A1 | 11/2018 | Chang et al. |
| 2018/0311136 | A1 | 11/2018 | Chang et al. |
| 2018/0325791 | A1 | 11/2018 | Lane et al. |
| 2018/0360716 | A1 | 12/2018 | Chang et al. |
| 2019/0035149 | A1 | 1/2019 | Chen |
| 2019/0105243 | A1 | 4/2019 | Song et al. |
| 2019/0105244 | A1 | 4/2019 | Song et al. |
| 2019/0105245 | A1 | 4/2019 | Song et al. |
| 2019/0117543 | A1 | 4/2019 | Zhao et al. |
| 2019/0313637 | A1 | 10/2019 | Seelmann-eggebert et al. |
| 2019/0343894 | A1 | 11/2019 | Pierce |
| 2019/0350514 | A1 | 11/2019 | Purwar |
| 2019/0350819 | A1 | 11/2019 | Hamersky |
| 2019/0355115 | A1 | 11/2019 | Niebauer |
| 2019/0375759 | A1 | 12/2019 | Ghosh et al. |
| 2019/0381055 | A1 | 12/2019 | Cong |
| 2020/0000690 | A1 | 1/2020 | Renock et al. |
| 2020/0061018 | A1 | 2/2020 | Lawyer et al. |
| 2020/0085863 | A1 | 3/2020 | Liu |
| 2020/0163334 | A1 | 5/2020 | Albright et al. |
| 2020/0163905 | A1 | 5/2020 | Mendrok-edinger et al. |
| 2020/0214953 | A1 | 7/2020 | Lane |
| 2021/0069091 | A1 | 3/2021 | Oh et al. |
| 2021/0283131 | A1 | 9/2021 | Richards et al. |
| 2021/0401707 | A1 | 12/2021 | Johnson et al. |
| 2021/0401710 | A1 | 12/2021 | Johnson et al. |
| 2021/0401818 | A1 | 12/2021 | Richards et al. |
| 2022/0160606 | A1 | 5/2022 | Renock |
| 2022/0202677 | A1 | 6/2022 | Stephens et al. |
| 2022/0312766 | A1 | 10/2022 | Nakamura et al. |

FOREIGN PATENT DOCUMENTS

| | | | |
|---|---|---|---|
| CN | 101755739 | A | 6/2010 |
| CN | 102715187 | A | 10/2012 |
| CN | 104000749 | B | 9/2016 |
| CN | 107595657 | A | 1/2018 |
| CN | 109620896 | A | 4/2019 |
| CN | 109700877 | A | 5/2019 |
| CN | 109757493 | A | 5/2019 |
| CN | 110025658 | A | 7/2019 |
| CN | 110420131 | A | 11/2019 |
| DE | 102012203240 | A1 | 3/2013 |
| DE | 102012220148 | A1 | 5/2014 |
| EP | 3801774 | B1 | 11/2021 |
| JP | 2009057387 | A | 3/2009 |
| KR | 1020120018739 | A | 3/2012 |
| WO | 9939683 | A1 | 8/1999 |
| WO | 0012059 | A1 | 3/2000 |
| WO | 0069410 | A1 | 11/2000 |
| WO | 0200027 | A1 | 1/2002 |
| WO | 2012040804 | A2 | 4/2012 |
| WO | 2012058557 | A2 | 5/2012 |
| WO | 2014073456 | A1 | 5/2014 |
| WO | 2014165253 | A1 | 10/2014 |
| WO | 2014208162 | A1 | 12/2014 |
| WO | 2016146361 | A1 | 9/2016 |
| WO | 2017009206 | A1 | 1/2017 |
| WO | 2019166521 | A1 | 9/2019 |
| WO | 2020264577 | A1 | 12/2020 |
| WO | 2021089306 | A1 | 5/2021 |

OTHER PUBLICATIONS

"Anti-Dandruff Treatment Hair Cream", Mintel, Sep. 3, 2018, 3 pgs.

"Balancing and Anti-Dandruff Shampoo", Mintel, Jan. 6, 2014, 3 pgs.

"Double Care Anti-Dandruff Treatment Hair Cream", Mintel, Oct. 16, 2012, 2 pgs.

"Hair Lotion", Mintel, Oct. 7, 2019, 3 pgs.

"Moist-Up Eye Cream", Mintel, Nov. 11, 2009, 5 Pgs.

"Moisturizing Anti-Dandruff Shampoo", Mintel, Mar. 17, 2016, 2 pgs.

Advanced Fungal Chemistry/Liu Jikai, editor. Beijing: China Science and Technology Press, 2004.6; ISBN 7-5046-3819-6, Year 2004, pp. 14.

All Office Actions; U.S. Appl. No. 16/412,745, filed May 15, 2019.

All Office Actions; U.S. Appl. No. 17/126,380, filed Dec. 18, 2020.

All Office Actions; U.S. Appl. No. 17/126,958, filed Dec. 18, 2020.

All Office Actions; U.S. Appl. No. 16/913,183, filed Jun. 26, 2020.

Andrew J. Wiemer et al., "A live imaging cell motility screen identifies prostaglandin E 2 as a T cell stop signal antagonist", The Journal of Immunology, vol. 187, No. 7, Oct. 1, 2011, 9 pgs.

Anonymous: "Mixtures of fungicides and insecticides", Research disclosure, Kenneth Mason Publications, Hampshire UK, GB, vol. 338, No. 93, Jun. 1, 1992, 9 pgs.

Anwar et al. "Size and shape dependent clinical and mycologícalefficacy of silver nanoparticles on dandruff", International Journal of Nanomedicine, 2016, pp. 147-161.

C. C. Zouboulis et al. "Acne is an inflammatory disease and alterations of sebumcomposition initiate acne lesions", J Eur Acad Dermatol Venereol, 2014, vol. 28, Issue5, pp. 527-532.

Hyun Seung Wi et al., "The anti-fungal effect of light emitting diode on yeasts", Journal of Dermatological Science, vol. 67, No. 1, Apr. 4, 2012, pp. 3-8.

K. J. Mills et al. "Dandruff/seborrhoeic dermatitis is characterized by aninflammatory genomic signature and possible immunedysfunction: transcriptional analysis of the condition andtreatment effects of zinc pyrithione", British Journal of Dermatology, 2012 vol. 166, pp. 33-40.

P. Mondon et al. "Reinforcement of barrier function and scalp homeostasis by Senkyunolide A to fight against dandruff", International Journal of Cosmetic Science, 2017, vol. 39, pp. 617-621.

Paterson "Salicylic acid: a link between aspirin, diet and the prevention of colorectal cancer", QJM, Aug. 2001. vol. 94(8); pp. 2.

(56) References Cited

OTHER PUBLICATIONS

Pierard-Franchimont C et al: "Effect ofresidence time on the efficacy of antidandruff shampoos", International Journal of Cosmetic Science,Jun. 30, 2003 (Jun. 30, 2003), XP055794760,DOI: 10.IIII/j.1467-2494.2003.00195.x Retrieved from the Internet:URL:https://doi.org/10.IIII/j.1467-2494.2003.00195.x[retrieved on Apr. 13, 2021] "Introduction" 6 pgs.
Pierard-Franchimont C, et al., "Revisiting dandruff", International Journal of Cosmetic Science, Kluwer Academic Publishers, Dordrecht, NL, vol. 28, No. 5, Oct. 1, 2006, pp. 311-318.
Research and Introduction of Biopesticides / Authors: Yang Ye, Harbin: Hellongjiang Science and Technology Press, Publication Date: Dec. 2008; ISBN: 978-7-5388-5888-4, 07 Pages.
Safety and Technical Standards for Cosmetics, Year 2015, pp. 02.
Schwartz et al., "The role of oxidative damage in poor scalp health: ramifications to causality and associated hair growth", International Journal of Cosmetic Science, vol. 37, No. Suppl. 2, 2015, pp. 9-15.
Turner et al. "Stratum Corneum Dysfunction in Dandruff", International Journal of Cosmetic Science, 34, Feb. 24, 2012, pp. 298-306.

SYNERGISTIC ANTIOXIDANT COMPOSITIONS

FIELD OF THE INVENTION

The present invention relates to personal care compositions comprising a hydroxy pyridone, niacinamide and panthenol demonstrating synergistic antioxidant activity.

BACKGROUND OF THE INVENTION

The skin is a complex organ in which the overall condition is directly impacted by the oxidative balance. There are many endogenous and exogenous sources of oxidizing species which the skin attempts to counteract with a series of endogenous antioxidant enzymes (such as superoxide dismutase). When the level of oxidizing species is greater than can be counteracted by the skin, the imbalance is called oxidative stress. There are numerous detrimental effects of oxidative stress, such as oxidized lipids and proteins that lead to compromised skin function, such as decreased barrier effectiveness. This can lead to skin dryness, excessive flaking, itch, and hair loss.

The sources of oxidative stress include those of exogenous origin such as pollution, cigarette smoke, ultraviolet light and certain product exposures. Sources of endogenous reactive oxygen species (ROS) include the effects of aging as well as those originating from microbial metabolism. The scalp is an especially susceptible portion of the skin. *Malassezia* fungi are a known source of ROS. Ultraviolet light exposure is also difficult to avoid on the scalp.

Antioxidants are materials that can supplement the body's ability to defend against ROS. These beneficial agents can be delivered orally or topically. For skin benefits, direct topical delivery is desired.

Between increasing environmental ROS sources and decreasing ability to counteract them in an aging population, there is a need for more effective topically delivered antioxidant materials. While there is a wide range of individual antioxidants available, unique combinations have the potential to result in synergistic activities, wherein the delivered activity is more than the sum of individual components. Binary synergies are challenging to identify, ternary synergies are even more unique. Such combinations are especially useful to supplement the body's native antioxidant activity.

SUMMARY OF THE INVENTION

The present invention is directed to a personal care composition comprising a hydroxy pyridone; niacinamide; and panthenol; wherein when the hydroxy pyridone is at about 0.8%, there is a synergistic antioxidant activity when niacinamide is from about 0.005% to about 0.1% and panthenol is from about 0.005% to about 0.2%.

DETAILED DESCRIPTION OF THE INVENTION

Figure 1:
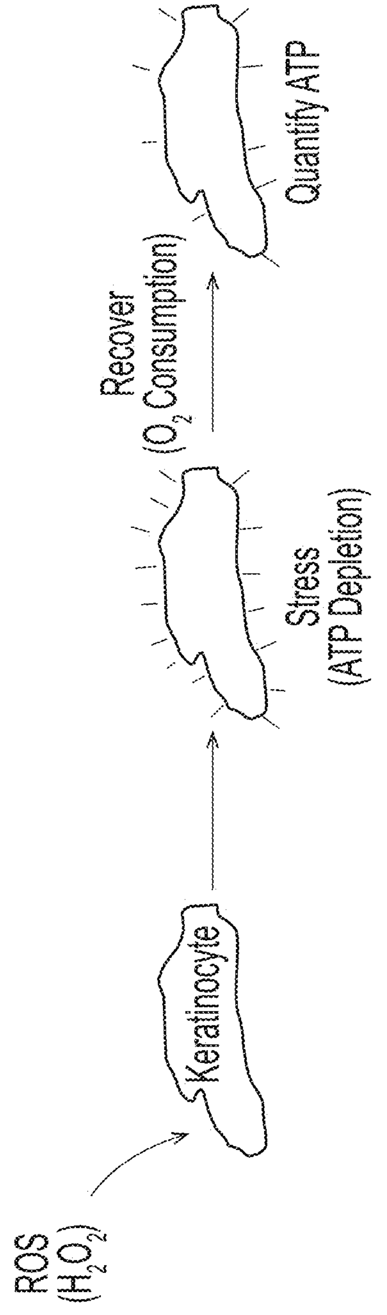
FIG. 1 depicts a schematic of Peroxide-Induced Keratinocyte Stress.
Figure 2:
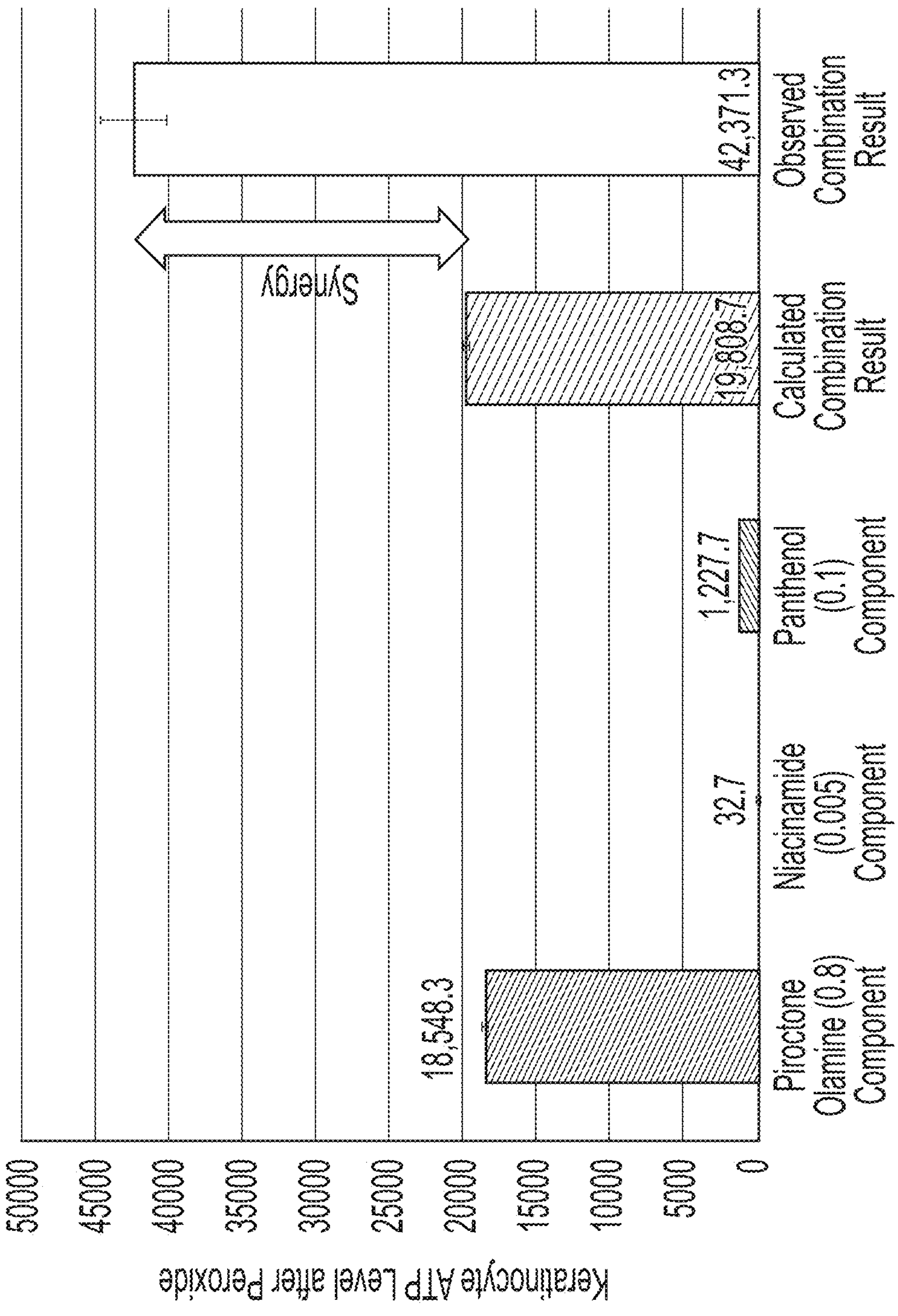
FIG. 2 depicts a Peroxide-Induced Keratinocyte Stress assay demonstrating a synergistic level of activity for the triad over the calculated sum of individual observations and is a graphical representation of the synergy data representing the ingredient levels of the shampoo.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Synergy is defined as occurring when two or more substances produce a combined effect greater than the sum of their separate effects. Binary synergies involve two components whereas ternary synergies involve three components.

Where amount ranges are given, these are to be understood as being the total amount of said ingredient in the composition, or where more than one species fall within the scope of the ingredient definition, the total amount of all ingredients fitting that definition, in the composition. All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

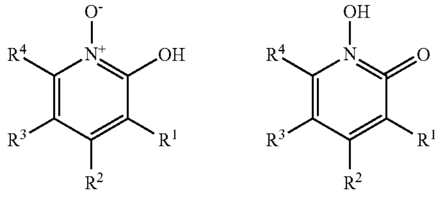

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $^+N(R^7R^8R^9R^{10})$, and 1/q $M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, ½ $Mg^{2+}$, or ½ $Ca^{2+}$, substituted ammonium, such as $C_1$-$C_6$ alkanolammnonium, mono-ethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4, 6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, MO) and/or Aces Pharma (Branford, CT).

In certain aspects, the 2-pyridinol-N-oxide material is a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, MO), Princeton Building Blocks (Monmouth Junction, NJ), 3B Scientific Corporation (Libertyville, IL), SynFine Research (Richmond Hill, ON), Ryan Scientific, Inc. (Mt. Pleasant, SC), and/or Aces Pharma (Branford, CT).

In certain aspects, the 2-pyridinol-N-oxide material is a 2-pyridinol-N-oxide material or tautomer thereof according to the formula(s) below:

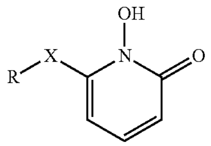

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

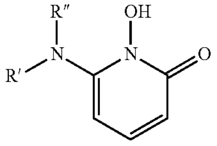

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt. The present invention may comprise a hydroxy pyridone. Further, the present invention may comprise a hydroxy pyridone which is piroctone olamine. Nonlimiting examples of hydroxy pyridones may include octopirox (piroctone olamine), ciclopirox, and rilopirox.

In the present invention, the hair care composition may contain from about 0.1% to about 10% of a hydroxy pyridone. Alternatively, the hair care composition may contain from about 0.3% to about 3% of a hydroxy pyridone. Alternatively, the hair care composition may contain from about 0.5% to about 2% of a hydroxy pyridone.

Niacinamide

Niacinamide has been shown to inhibit the oxidative damage caused by pollutant particulate matter as well as lipoperoxide generation in skin.

Vitamin $B_3$ Compounds The compositions of the present invention can include a vitamin B3 compound. Vitamin B3 compounds are particularly useful for regulating skin conditions. The composition of the present invention may contain from about 0.001% to about 5% of a vitamin B3 compound; may contain from about 0.005% to about 3% of a vitamin B3 compound; may contain from about 0.01% to about 2% of a vitamin B3 compound. As used herein, "vitamin B3 compound" means a one or more compounds having the formula:

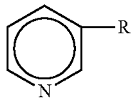

wherein R is —$CONH_2$ (i.e., niacinamide), —COOH (i.e., nicotinic acid) or —CH2OH (i.e., nicotinyl alcohol); derivatives thereof; mixtures thereof; and salts of any of the foregoing.

Exemplary derivatives of the foregoing vitamin B3 compounds include nicotinic acid esters, including non-vasodilating esters of nicotinic acid (e.g, tocopherol nicotinate, myristyl nicotinate), nicotinyl amino acids, nicotinyl alcohol esters of carboxylic acids, nicotinic acid N-oxide and niacinamide N-oxide.

Suitable esters of nicotinic acid include nicotinic acid esters of $C_1$-$C_{22}$, may be $C_1$-$C_{16}$, may be $C_1$-$C_6$ alcohols. The alcohols are suitably straight-chain or branched chain, cyclic or acyclic, saturated or unsaturated (including aromatic), and substituted or unsubstituted. The esters may be non-vasodilating. As used herein, "non-vasodilating" means that the ester does not commonly yield a visible flushing response after application to the skin in the subject compositions (the majority of the general population would not experience a visible flushing response, although such compounds may cause vasodilation not visible to the naked eye, i.e., the ester is non-rubifacient). Non-vasodilating esters of nicotinic acid may include tocopherol nicotinate and inositol hexanicotinate; may be tocopherol nicotinate.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1-C18). Specific examples of such derivatives include nicotinuric acid (C8H8N2O3) and nicotinyl hydroxamic acid (C6H6N2O2), which have the following chemical structures:

nicotinuric acid:

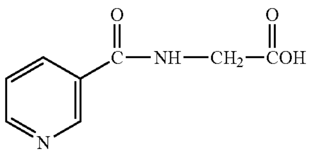

-continued nicotinyl hydroxamic acid:

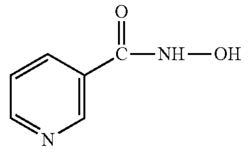

Exemplary nicotinyl alcohol esters include nicotinyl alcohol esters of the carboxylic acids salicylic acid, acetic acid, glycolic acid, palmitic acid and the like. Other non-limiting examples of vitamin B3 compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin B3 compounds are well known in the art and are commercially available from a number of sources, e.g., the Sigma Chemical Company (St. Louis, MO); ICN Biomedicals, Inc. (Irvin, CA) and Aldrich Chemical Company (Milwaukee, WI).

One or more vitamin B3 compounds may be used herein. In the present invention, vitamin B3 compounds may be niacinamide and tocopherol nicotinate. In the present invention, vitamin B3 may be Niacinamide. The composition of the present invention may contain from about 0.001% to about 5% of niacinamide; may contain from about 0.005% to about 3% of niacinamide; may contain from about 0.01% to about 2% of niacinamide.

When used, salts, derivatives, and salt derivatives of niacinamide may be those having substantially the same efficacy as niacinamide.

Salts of the vitamin B3 compound are also useful herein. Nonlimiting examples of salts of the vitamin B3 compound useful herein include organic or inorganic salts, such as inorganic salts with anionic inorganic species (e.g., chloride, bromide, iodide, carbonate), and organic carboxylic acid salts (including mono-, di- and tri- C1-C18 carboxylic acid salts, e.g., acetate, salicylate, glycolate, lactate, malate, citrate, may be monocarboxylic acid salts such as acetate). These and other salts of the vitamin B3 compound can be readily prepared by the skilled artisan, for example, as described by W. Wenner, "The Reaction of L-Ascorbic and D-Iosascorbic Acid with Nicotinic Acid and Its Amide", J. Organic Chemistry, Vol. 14, 22-26 (1949). Wenner describes the synthesis of the ascorbic acid salt of niacinamide.

In the present invention, the ring nitrogen of the vitamin B3 compound may be substantially chemically free (e.g., unbound and/or unhindered), or after delivery to the skin becomes substantially chemically free ("chemically free" is hereinafter alternatively referred to as "uncomplexed"). In the present invention, the vitamin B3 compound may be essentially uncomplexed. Therefore, if the composition contains the vitamin B3 compound in a salt or otherwise complexed form, such complex may be substantially reversible, such complex may be essentially reversible, upon delivery of the composition to the skin. For example, such complex should be substantially reversible at a pH of from about 5.0 to about 6.0. Such reversibility can be readily determined by one having ordinary skill in the art.

In the present invention, the vitamin B3 compound may be substantially uncomplexed in the composition prior to delivery to the keratinous tissue. Exemplary approaches to minimizing or preventing the formation of undesirable complexes include omission of materials which form substantially irreversible or other complexes with the vitamin B3 compound, pH adjustment, ionic strength adjustment, the use of surfactants, and formulating wherein the vitamin B3 compound and materials which complex therewith are in different phases. Such approaches are well within the level of ordinary skill in the art.

Thus, in the present invention, the vitamin B3 compound may contain a limited amount of the salt form and in the present invention, may be substantially free of salts of a vitamin B3 compound. In the present invention the vitamin B3 compound may contain less than about 50% of such salt, and in the present invention may be essentially free of the salt form. The vitamin B3 compound in the compositions hereof having a pH of from about 4 to about 7 typically contain less than about 50% of the salt form.

The vitamin B3 compound may be included as the substantially pure material, or as an extract obtained by suitable physical and/or chemical isolation from natural (e.g., plant) sources. In the present invention, the vitamin B3 compound may be substantially pure. In the present invention, the vitamin B3 compound may be essentially pure.

Panthenol

Panthenol has been shown to inhibit the formation of reactive oxygen species (ROS) in skin fibroblasts in vitro.

The compositions of the present invention may comprise a panthenol compound. As used herein, the term "panthenol compound" is broad enough to include panthenol, one or more pantothenic acid derivatives, and mixtures thereof. Panthenol and its derivatives can include D-panthenol ([R]-2,4-dihydroxy-N-[3-hydroxypropyl)]-3,3-dimethylbutamide), DL-panthenol, pantothenic acids and their salts, may be the calcium salt, panthenyl triacetate, royal jelly, panthetine, pantotheine, panthenyl ethyl ether, pangamic acid, pantoyl lactose, Vitamin B complex, or mixtures thereof.

Compositions comprising pantothenic acid derivatives that remain more stable than panthenol and other similar materials in acidic compositions or in compositions containing acid-producing materials such as aluminum-containing actives, can also be suitable for use herein. The selected pantothenic acid derivatives are most typically in liquid form and dispersed throughout or otherwise solubilized within the liquid carrier component of the composition.

The term "pantothenic acid derivative" as used herein refers to those materials that conform to the formula:

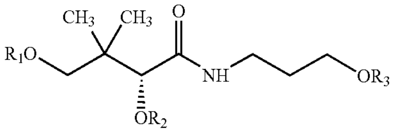

wherein $R_1$, $R_2$ and $R_3$ are hydrogen, C2-C20 hydrocarbons, C2-C20 carboxylic acid esters, or combinations thereof, provided that not more than two of R1, R2 and R3 are hydrogen. In one embodiment, $R_1$, $R_2$ and $R_3$ are independently selected from hydrogen, C2-C8 hydrocarbons, C2-C8 carboxylic acid esters, or combinations thereof; in another embodiment, $R_1$ and $R_2$ are hydrogen, and $R_3$ is a C2-C8 hydrocarbon, C2-C8 carboxylic acid ester, or combinations thereof; in yet another embodiment, $R_1$ and $R_2$ are hydrogen and $R_3$ is ethyl. The selected pantothenic acid derivatives may be derived or otherwise obtained from any known source, which may include pantothenic acid or materials other than pantothenic acid, so long as the resulting material has the above defined chemical formula.

Specific non-limiting examples of selected pantothenic acid derivatives for use herein include ethyl panthenol, panthenyl triacetate, and combinations thereof. In a particular embodiment, a pantothenic acid derivative comprises the d-isomeric form(s) of such derivative form(s), such as d-ethyl panthenol.

The composition of the present invention may contain from about 0.001% to about 3% of panthenol; may contain from about 0.005% to about 1% of panthenol; may contain from about 0.005% to about 0.5% of panthenol; may contain from about 0.005% to about 0.2% of panthenol.

Methods

Peroxide-Induced Keratinocyte Stress

The principle used in this in vitro cellular methodology is oxidatively stress keratinocytes, which depletes their cellular energy (ATP) and then to quantify the ability of various materials to inhibit the negative consequences of the oxidative stress (higher ATP is more effective) and as demonstrated in FIG. 1.

This methodology is further discussed in Assessing bioenergetic function in response to oxidative stress by metabolic profiling. Free Radical Biology and Medicine; Dranka B P, Benavides G A, Diers A R, Giordano S, Zelickson B R, Reily C. Zou L, Chatham J C, Hill B G, Zhang J, Landar A; 2011 Nov. 1; 51(9):1621-35, incorporated herein by reference, as well as in Proceedings of the National Academy of Sciences of the United States of America; Miyoshi N, Oubrahim H, Chock P B, Stadtman E R . . . 2006 Feb. 7; 103(6):1727-31, incorporated herein by reference.

Experimental Methodology: This method demonstrates the synergistic reduction in Adenosine Triphosphate (ATP) depletion caused by Reactive Oxygen Species (ROS). Hydrogen peroxide is a well-known ROS as is commonly used as a surrogate to analyze the effects of a variety of ROS. In this test, keratinocytes are cultured (passage <8) in T150 flasks using Epi-Life medium (Calcium Free and Phenol Red Free, supplemented with penicillin/streptomycin and keratinocytes growth supplement, Invitrogen cat #MEPICF-PRF500) in a CO2 incubator (Forma 51030532, Marietta OH). The keratinocytes are then plated into 96 well plates, 10,000 cells/well, 0.2 ml media. After 24 hours incubation in 37° C. in CO2 Incubator, the keratinocytes are treated with 500 uM hydrogen peroxide alone and with (for example) 0.0000061 w/v % of zinc pyrithione, 0.0000061 w/v % of piroctone olamine, 0.0000097 w/v % of zinc carbonate individually and all together in combination for 1 hour. The keratinocytes are washed in PBS and ATP levels are measured using the Cell Titer-Glo® system (Promega cat #G7571/2/3, Madison, WI) per manufacturer's directions. Luminescence is measured on a SpectraMax M3 (Molecular Devices, Sunnyvale, CA). Net luminescence is calculated by subtracting the luminescence counts from the vehicle control from the luminescence counts from the treatment groups. Synergy is defined by the observed luminescence value from the triple combination exceeding (with p-value<0.05) the sum of luminescence values of each individual component.

Results

The ATP levels post-peroxide exposure is measured for the individual materials as well as the triple combination within the following ranges:

| Material | Low Level (%) | High Level (%) |
|---|---|---|
| Piroctone Olamine | 0.5 | 0.8 |
| Niacinamide | 0.005 | 1.8 |
| Panthenol | 0.005 | 0.2 |

In each case, the arithmetic sum of the measured anti-oxidant activity of the three individual components is compared to the measured anti-oxidant activity of the triad combination of the same levels. Experiments are done in triplicate enabling the statistical determination (by T-test) of significance of whether synergism (observed/calculated ratio is greater than 1) is observed. Synergism is defined as a significantly (greater than or equal to 95% confidence) higher observed ATP level for the combination vs. the sum of the three individual components. The full data is summarized in the table below:

Summary of ATP Levels Post-Peroxide Exposure

| Composition (%) | | | Mean Keratinocyte ATP Level | | | Triad Combination | | | |
|---|---|---|---|---|---|---|---|---|---|
| Piroctone Olamine | Nia-cinamide | Panthenol | Piroctone Olamine | Nia-cinamide | Panthenol | Calculated | Observed | Ratio (Obs/Cal) | p-value |
| 0.8 | 1.8 | 0.2 | 18548.3 | 11751.3 | 5711.7 | 36011.3 | 33674.3 | 0.94 | 0.0208 |
| 0.8 | 1.8 | 0.1 | 18548.3 | 11751.3 | 1227.7 | 31527.3 | 28629.3 | 0.91 | 0.0128 |
| 0.8 | 1.8 | 0.05 | 18548.3 | 11751.3 | 550.7 | 30850.3 | 27491.3 | 0.89 | 0.0074 |
| 0.8 | 1.8 | 0.01 | 18548.3 | 11751.3 | 280.0 | 30579.7 | 27384.0 | 0.90 | 0.0110 |
| 0.8 | 1.8 | 0.005 | 18548.3 | 11751.3 | 170.0 | 30469.7 | 26976.0 | 0.89 | 0.0076 |
| 0.8 | 1.0 | 0.2 | 18548.3 | 6003.7 | 5711.7 | 30263.7 | 30222.7 | 1.00 | 0.9529 |
| 0.8 | 1.0 | 0.1 | 18548.3 | 6003.7 | 1227.7 | 25779.7 | 28408.0 | 1.10 | 0.1225 |
| 0.8 | 1.0 | 0.05 | 18548.3 | 6003.7 | 550.7 | 25102.7 | 26261.0 | 1.05 | 0.2198 |
| 0.8 | 1.0 | 0.01 | 18548.3 | 6003.7 | 280.0 | 24832.0 | 26219.7 | 1.06 | 0.1414 |
| 0.8 | 1.0 | 0.005 | 18548.3 | 6003.7 | 170.0 | 24722.0 | 25871.3 | 1.05 | 0.4679 |
| 0.8 | 0.1 | 0.2 | 18548.3 | 875.0 | 5711.7 | 25135.0 | 33029.3 | ***1.31*** | 0.0016 |
| 0.8 | 0.1 | 0.1 | 18548.3 | 875.0 | 1227.7 | 20651.0 | 27730.7 | ***1.34*** | 0.0004 |
| 0.8 | 0.1 | 0.05 | 18548.3 | 875.0 | 550.7 | 19974.0 | 27515.0 | ***1.38*** | 0.0001 |
| 0.8 | 0.1 | 0.01 | 18548.3 | 875.0 | 280.0 | 19703.3 | 28122.3 | ***1.43*** | 0.0002 |
| 0.8 | 0.1 | 0.005 | 18548.3 | 875.0 | 170.0 | 19593.3 | 25681.7 | ***1.31*** | 0.0007 |
| 0.8 | 0.05 | 0.2 | 18548.3 | 465.0 | 5711.7 | 24725.0 | 31880.3 | ***1.29*** | 0.0077 |
| 0.8 | 0.05 | 0.1 | 18548.3 | 465.0 | 1227.7 | 20241.0 | 34877.3 | ***1.72*** | 0.0000 |
| 0.8 | 0.05 | 0.05 | 18548.3 | 465.0 | 550.7 | 19564.0 | 37752.3 | ***1.93*** | 0.0001 |
| 0.8 | 0.05 | 0.01 | 18548.3 | 465.0 | 280.0 | 19293.3 | 34956.3 | ***1.81*** | 0.0000 |

-continued

| Composition (%) | | | Mean Keratinocyte ATP Level | | | Triad Combination | | | |
|---|---|---|---|---|---|---|---|---|---|
| Piroctone Olamine | Nia-cinamide | Panthenol | Piroctone Olamine | Nia-cinamide | Panthenol | Calculated | Observed | Ratio (Obs/Cal) | p-value |
| 0.8 | 0.05 | 0.005 | 18548.3 | 465.0 | 170.0 | 19183.3 | 36254.0 | ***1.89*** | 0.0001 |
| 0.8 | 0.01 | 0.2 | 18548.3 | 85.7 | 5711.7 | 24345.7 | 32212.7 | ***1.32*** | 0.0012 |
| 0.8 | 0.01 | 0.1 | 18548.3 | 85.7 | 1227.7 | 19861.7 | 37747.0 | ***1.90*** | 0.0001 |
| 0.8 | 0.01 | 0.05 | 18548.3 | 85.7 | 550.7 | 19184.7 | 38913.0 | ***2.03*** | 0.0000 |
| 0.8 | 0.01 | 0.01 | 18548.3 | 85.7 | 280.0 | 18914.0 | 41021.3 | ***2.17*** | 0.0000 |
| 0.8 | 0.01 | 0.005 | 18548.3 | 85.7 | 170.0 | 18804.0 | 37145.3 | ***1.98*** | 0.0001 |
| 0.8 | 0.005 | 0.2 | 18548.3 | 32.7 | 5711.7 | 24292.7 | 34494.0 | ***1.42*** | 0.0006 |
| 0.8 | 0.005 | 0.1 | 18548.3 | 32.7 | 1227.7 | 19808.7 | 42371.3 | ***2.14*** | 0.0001 |
| 0.8 | 0.005 | 0.05 | 18548.3 | 32.7 | 550.7 | 19131.7 | 43005.7 | ***2.25*** | 0.0000 |
| 0.8 | 0.005 | 0.01 | 18548.3 | 32.7 | 280.0 | 18861.0 | 40897.3 | ***2.17*** | 0.0000 |
| 0.5 | 1.8 | 0.2 | 13548.3 | 12314.3 | 5282.0 | 31144.7 | 31035.3 | 1.00 | 0.6518 |
| 0.5 | 1.8 | 0.1 | 13548.3 | 12314.3 | 1234.3 | 27097.0 | 28371.7 | 1.05 | 0.1924 |
| 0.5 | 1.8 | 0.05 | 13548.3 | 12314.3 | 617.3 | 26480.0 | 27397.0 | 1.03 | 0.3062 |
| 0.5 | 1.8 | 0.01 | 13548.3 | 12314.3 | 473.3 | 26336.0 | 27778.7 | 1.05 | 0.1076 |
| 0.5 | 1.8 | 0.005 | 13548.3 | 12314.3 | 193.3 | 26056.0 | 27824.7 | 1.07 | 0.0858 |
| 0.5 | 1.0 | 0.2 | 13548.3 | 9208.3 | 5282.0 | 28038.7 | 29368.7 | 1.05 | 0.3135 |
| 0.5 | 1.0 | 0.1 | 13548.3 | 9208.3 | 1234.3 | 23991.0 | 25350.7 | 1.06 | 0.1622 |
| 0.5 | 1.0 | 0.05 | 13548.3 | 9208.3 | 617.3 | 23374.0 | 24142.0 | 1.03 | 0.1736 |
| 0.5 | 1.0 | 0.01 | 13548.3 | 9208.3 | 473.3 | 23230.0 | 24445.3 | 1.05 | 0.1568 |
| 0.5 | 1.0 | 0.005 | 13548.3 | 9208.3 | 193.3 | 22950.0 | 33824.7 | ***1.47*** | 0.0001 |
| 0.5 | 0.1 | 0.2 | 13548.3 | 1142.0 | 5282.0 | 19972.3 | 20935.3 | 1.05 | 0.0947 |
| 0.5 | 0.1 | 0.1 | 13548.3 | 1142.0 | 1234.3 | 15924.7 | 16371.7 | 1.03 | 0.5484 |
| 0.5 | 0.1 | 0.05 | 13548.3 | 1142.0 | 617.3 | 15307.7 | 22341.0 | ***1.46*** | 0.0007 |
| 0.5 | 0.1 | 0.01 | 13548.3 | 1142.0 | 473.3 | 15163.7 | 24375.3 | ***1.61*** | 0.0005 |
| 0.5 | 0.1 | 0.005 | 13548.3 | 1142.0 | 193.3 | 14883.7 | 24991.3 | ***1.68*** | 0.0001 |
| 0.5 | 0.05 | 0.2 | 13548.3 | 341.0 | 5282.0 | 19171.3 | 20035.3 | 1.05 | 0.4341 |
| 0.5 | 0.05 | 0.1 | 13548.3 | 341.0 | 1234.3 | 15123.7 | 22371.7 | ***1.48*** | 0.0003 |
| 0.5 | 0.05 | 0.05 | 13548.3 | 341.0 | 617.3 | 14506.7 | 22011.3 | ***1.52*** | 0.0007 |
| 0.5 | 0.05 | 0.01 | 13548.3 | 341.0 | 473.3 | 14362.7 | 23778.7 | ***1.66*** | 0.0001 |
| 0.5 | 0.05 | 0.005 | 13548.3 | 341.0 | 193.3 | 14082.7 | 27324.7 | ***1.94*** | 0.0000 |
| 0.5 | 0.01 | 0.2 | 13548.3 | 154.3 | 5282.0 | 18984.7 | 28702.0 | ***1.51*** | 0.0000 |
| 0.5 | 0.01 | 0.1 | 13548.3 | 154.3 | 1234.3 | 14937.0 | 28705.0 | ***1.92*** | 0.0000 |
| 0.5 | 0.01 | 0.05 | 13548.3 | 154.3 | 617.3 | 14320.0 | 29307.7 | ***2.05*** | 0.0000 |
| 0.5 | 0.01 | 0.01 | 13548.3 | 154.3 | 473.3 | 14176.0 | 30978.7 | ***2.19*** | 0.0001 |
| 0.5 | 0.01 | 0.005 | 13548.3 | 154.3 | 193.3 | 13896.0 | 32024.7 | ***2.30*** | 0.0001 |
| 0.5 | 0.005 | 0.2 | 13548.3 | 100.3 | 5282.0 | 18930.7 | 40702.0 | ***2.15*** | 0.0000 |
| 0.5 | 0.005 | 0.1 | 13548.3 | 100.3 | 1234.3 | 14883.0 | 32038.3 | ***2.15*** | 0.0002 |
| 0.5 | 0.005 | 0.05 | 13548.3 | 100.3 | 617.3 | 14266.0 | 34307.7 | ***2.40*** | 0.0000 |
| 0.5 | 0.005 | 0.01 | 13548.3 | 100.3 | 473.3 | 14122.0 | 36778.7 | ***2.60*** | 0.0000 |
| 0.5 | 0.005 | 0.005 | 13548.3 | 100.3 | 193.3 | 13842.0 | 36491.3 | ***2.64*** | 0.0000 |

The below tables summarize the compositional domains (in BOLD italic type) which demonstrates a statistically significant synergy (observed/calculated ratio is greater than 1), represented as the ratio between observed and calculated combination results (separated into two PO levels):

Synergy Factor (combo observed/combo expected)
PO 0.8%

| | | Panthenol (%) | | | | |
|---|---|---|---|---|---|---|
| | | 0.2 | 0.1 | 0.05 | 0.01 | 0.005 |
| Niacinamide (%) | 1.8 | 0.94 | 0.91 | 0.89 | 0.90 | 0.89 |
| | 1.0 | 1.00 | 1.10 | 1.05 | 1.06 | 1.05 |
| | 0.1 | ***1.31*** | ***1.34*** | ***1.38*** | ***1.43*** | ***1.31*** |
| | 0.05 | ***1.29*** | ***1.72*** | ***1.93*** | ***1.81*** | ***1.89*** |
| | 0.01 | ***1.32*** | ***1.90*** | ***2.03*** | ***2.17*** | ***1.98*** |
| | 0.005 | ***1.42*** | ***2.14*** | ***2.25*** | ***2.17*** | ***1.98*** |

Synergy Factor (combo observed/combo expected)
PO 0.5%

| | | Panthenol (%) | | | | |
|---|---|---|---|---|---|---|
| | | 0.2 | 0.1 | 0.05 | 0.01 | 0.005 |
| Niacinamide (%) | 1.8 | 1.00 | 1.05 | 1.03 | 1.05 | 1.07 |
| | 1.0 | 1.05 | 1.06 | 1.03 | 1.05 | ***1.47*** |
| | 0.1 | 1.05 | 1.03 | ***1.46*** | ***1.61*** | ***1.68*** |
| | 0.05 | 1.05 | ***1.48*** | ***1.52*** | ***1.66*** | ***1.94*** |
| | 0.01 | ***1.51*** | ***1.92*** | ***2.05*** | ***2.19*** | ***2.30*** |
| | 0.005 | ***2.15*** | ***2.15*** | ***2.40*** | ***2.60*** | ***2.64*** |

Results: As demonstrated in the above table, the results upon application of this method are shown for synergistic level of activity (in BOLD italic type) for the triad over the calculated sum of individual observations. The results demonstrate that when piroctone olamine is at 0.8%, synergy is observed when niacinamide is from about 0.005% to about 0.1% and panthenol is from about 0.005% to about 0.2%.

The results demonstrate that when piroctone olamine is at 0.5%, synergy is observed when panthenol is at 0.005% and niacinamide is from about 0.005% to about 1%; or when panthenol is from about 0.01% to about 0.05% and niacinamide is from about 0.005% to about 0.1%; or when panthenol is at 0.1% and niacinamide is from about 0.005% to about 0.05%; or when panthenol is at 0.005% and niacinamide is from about 0.005% to about 0.01%.

The results demonstrate that when piroctone olamine is from about 0.5% to about 0.8%, synergy is observed when panthenol is from about 0.005% to about 0.05% and niacinamide is from about 0.005% to about 0.1%; or when panthenol is at 0.1% and niacinamide is from about 0.005% to about 0.05%; or when panthenol is at 0.2% and niacinamide is from about 0.005% to about 0.01%.

While the results above demonstrate synergy at either 0.5% or 0.8% concentrations of piroctone olamine, it is reasonable to assume that synergy would also occur between these two levels of piroctone olamine, at similar concentrations of niacinamide and panthenol.

Detersive Surfactant

The present invention may be present in the form of a shampoo, conditioner, or leave on treatment. The shampoo composition may comprise one or more detersive surfactants, which provides cleaning performance to the composition. The one or more detersive surfactants in turn may comprise an anionic surfactant, amphoteric or zwitterionic surfactants, or mixtures thereof.

Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Further, zwitterionics such as betaines may be selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Conditioner Composition

The conditioner composition described herein comprises (i) from about 0.025% to about 0.25%, alternatively from about 0.05% to about 0.2%, alternatively from about 0.1% to about 0.15% histidine, by weight of the conditioner composition, and (ii) a conditioner gel matrix. After applying to the hair a conditioner composition as described herein, the method then comprises rinsing the conditioner composition from the hair. The conditioner composition also comprises a conditioner gel matrix comprising (1) one or more high melting point fatty compounds, (2) a cationic surfactant system, and (3) a second aqueous carrier.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and may be a C22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

(I)

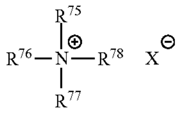

(I)

wherein one of $R^{75}$, $R^{76}$, $R^{77}$ and $R^{78}$ is selected from an alkyl group of 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of about 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as ℓ-glutamic acid, lactic acid, hydrochloric acid, malic acid, succinic acid, acetic acid, fumaric acid, tartaric acid, citric acid, ℓ-glutamic hydrochloride, maleic acid, and mixtures thereof; further, may be ℓ-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

(II)

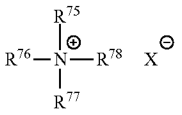

wherein two of $R^{75}$, $R^{76}$, $R^{77}$ and $R^{78}$ is selected from an alkyl group of from 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of from 22 carbon atoms, the remainder of $R^{75}$, $R^{76}$, $R^{77}$ and $R^{78}$ are independently selected from $CH_3$, $C_2H_5$, $C_2H_4OH$, and mixtures thereof;

and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (C22) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Additional Components

The shampoo composition, conditioner compositions, and/or leave-on treatments described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Thickening Polymers

The hair care composition may comprise a thickening polymer to increase the viscosity of the composition. Suitable thickening polymers can be used. The hair care composition may comprise from about 0.25% to about 10% of a thickening polymer, from about 0.5% to about 8% of a thickening polymer, from about 1.0% to about 5% of a thickening polymer, and from about 1% to about 4% of a thickening polymer. The thickening polymer modifier may be a polyacrylate, polyacrylamide thickeners. The thickening polymer may be an anionic thickening polymer.

The hair care composition may comprise thickening polymers that are homopolymers based on acrylic acid, methacrylic acid or other related derivatives, non-limiting examples include polyacrylate, polymethacrylate, polyethylacrylate, and polyacrylamide.

The thickening polymers may be alkali swellable and hydrophobically-modified alkali swellable acrylic copolymers or methacrylate copolymers, non-limiting examples include acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer.

The thickening polymers may be soluble crosslinked acrylic polymers, a non-limiting example includes carbomers.

The thickening polymers may be an associative polymeric thickeners, non-limiting examples include: hydrophobically modified, alkali swellable emulsions, non-limiting examples include hydrophobically modified polypolyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof.

Non-limiting examples of thickening polymers include acrylamide/ammonium acrylate copolymer (and) polyisobutene (and) polysorbate 20; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Taurate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; carbomer, sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, Acrylamide/Sodium Acryloyldimethyltaurate/Acrylic Acid Copolymer, sodium acrylate/acryloyldimethyltaurate/dimethylacrylamide, crosspolymer (and) isohexadecane (and) polysorbate 60, sodium polyacrylate. Exemplary commercially-available thickening polymers include ACULYN™ 28, ACULYN™ 33, ACULYN™ 88, ACULYN™ 22, ACULYN™ Excel, FlexiThix™, Carbopol® Aqua SF-1, Carbopol® ETD 2020, Carbopol® Ultrez 20, Carbopol® Ultrez 21, Carbopol® Ultrez 10, Carbopol® Ultrez 30, Carbopol® 1342, Carbopol® Aqua SF-2 Polymer, Sepigel™ 305, Simulgel™ 600, Sepimax Zen, Carbopol® SMART 1000, Rheocare® TTA, Rheomer® SC-Plus, STRUCTURE® PLUS, Aristoflex® AVC, Stabylen 30 and combinations thereof.

Benefit Agents

The hair care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, and treatment products; and any other form that may be applied to hair.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

EXAMPLES

Non-Limiting Examples

The following examples further describe and demonstrate non-limiting within the scope of the present invention. The examples are prepared by conventional formulation and mixing methods. All exemplified amounts are listed as weight percent on an active basis and exclude minor materials such as diluents, preservatives, color solutions, imagery ingredients, botanicals, and so forth, unless otherwise specified. All percentages are based on weight unless otherwise specified. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Shampoo Compositions

| | Example, active wt % | | | |
|---|---|---|---|---|
| Ingredients | 1 | 2 | 3 | 4 |
| Sodium Laureth-1 Sulfate [1] | 6.0 | 8.0 | 11.0 | 13.0 |
| Sodium Deceth-1 Sulfate [2] | 2.0 | 1.0 | 3.0 | 1.0 |
| Cocamidopropyl Betaine [3] | | 1.0 | | |
| Cocamide MEA [4] | | | | 0.25 |
| Piroctone Olamine [5] | 0.5 | 0.5 | 1.0 | 0.8 |
| Guar Hydroxypropyltrimonium Chloride [6] | | 0.5 | | |
| Guar Hydroxypropyltrimonium Chloride [7] | | | | |
| Guar Hydroxypropyltrimonium Chloride[8] | | | | 0.4 |
| Polyquaternium-76 [9] | 0.25 | | | |
| Polyquaternium-10 [10] | | | 0.45 | |
| Acrylates Copolymer [11] | 2.5 | 0.9 | | 0.7 |
| Panthenol[12] | | | | 0.1 |
| Niacinamide [13] | | | | 0.005 |
| Ginger Root Extract [14] | | | | 0.1 |
| Sodium Benzoate [15] | 0.25 | 0.25 | 0.25 | 0.25 |
| Tetrasodium EDTA [16] | 0.13 | 0.13 | 0.13 | |
| Methylchloroisothiazolinone/Methylisothiazolinone [17] | 5 ppm | | 5 ppm | |
| Salicylic Acid [18] | | 0.25 | | |
| Citric Acid [19] | Up to 2% | Up to 2% | Up to 2% | Up to 2% |
| Sodium Citrate [20] | Up to 2% | Up to 2% | Up to 2% | Up to 2% |
| Fragrance | 1.0 | 1.0 | 0.9 | 0.9 |
| Sodium Chloride [21] | Up to 3% | Up to 3% | Up to 3% | Up to 3% |
| Water | q.s. | q.s. | q.s. | q.s. |
| pH | 4.0 | 5.8 | 5.0 | 5.3 |

| | Example compositions | | | | |
|---|---|---|---|---|---|
| | 5 | 6 | 7 | 8 | 9 |
| Sodium Laureth Sulfate (SLE1S) (1) | | | | | |
| Sodium Lauryl Sulfate (2) | | | | | |
| Sodium Cocoyl isethionate (3) | | | | 6 | 6 |
| Sodium Lauroyl methyl isethionate (4) | 6 | 6 | 6 | | |
| Sodium Lauroyl Sarcosinate (5) | 4 | | | 4 | 4 |
| Lauramidopropyl Betaine (6) | 9.75 | 10.75 | 9.75 | | |
| Cocamidopropyl Betaine (7) | | | | 9.75 | 9.75 |
| Cocamide MEA (8) | | | | | |
| Acrylate copolymer (9) | 0.7 | 0.7 | 0.7 | 0.7 | 0.7 |
| Trihydroxystearin (10) | | | | | |
| Glycol Distearate (11) | | | | | |
| Piroctone Olamine (12) | 0.5 | 0.8 | 0.5 | 0.8 | 0.5 |
| Niacinamide (13) | 0.005 | 1.8 | 0.005 | 1.8 | 0.005 |
| Panthenol (14) | 0.005 | 0.005 | 0.2 | 0.2 | 0.2 |
| Polyquaternium-10 (15) | 0.6 | 0.6 | 0.6 | 0.6 | 0.25 |
| Guar Hyrdroxypropyltrimonium Chloride (LMW) (16) | | | | | |
| Guar Hyrdroxypropyltrimonium Chloride BF17 (HMW) (17) | | | | | |
| Polyquaternium-76 (18) | | | | | |
| Perfume (19) | 1 | 1 | 1 | 1 | 1 |
| Dimethicone DC 1872 (20) | 0.5 | 0.5 | 0.5 | 0.5 | 0.5 |
| Dimethicone DC330M (21) | | | | | |
| citric acid (22) | QS to pH 5 | QS to pH 5 | QS to pH 5.8 | QS to pH 5.8 | QS to pH 5.8 |
| Hydrochloric acid (23) | | | | | |
| Methylchloroisothiazolinone/ Methylisothiazolinone (24) | | | | | |

-continued

| | | | | | |
|---|---|---|---|---|---|
| Sodium Salicylate (25) | 0.15 | 0.15 | 0.15 | 0.15 | 0.15 |
| Sodium Chloride (26) | | | | | |
| Sodium Benzoate (27) | 0.25 | 0.25 | 0.25 | 0.25 | 0.25 |
| Water and Minors (QS to 100%) (28) | QS | QS | QS | QS | QS |

[1] Sodium Laureth-1 Sulfate at 26% active, supplier P&G

[2] Sodium Deceth-1 Sulfate at 34% active, supplier P&G

[3] Tego Betain L 7 OK at 30% active, supplier: Evonik

[4] Ninol Comf at 85% active, supplier: Stepan

[5] Octopirox, supplier: Clariant

[6] N-Hance BF-13: MW = 800,000 g/mol, CD = 1.1 meq/g, supplier: Ashland Specialty Ingredients

[7] Jaguar Excel: MW = 1,500,000 g/mol, CD = 0.7 meq/g, supplier Solvay

[8]N-Hance ™ 3196, Ashland

[9] Mirapol AT-1 at 10% active: MW = 1,100,000 g/mol, CD = 1.6 meq/g, supplier: Solvay

[10] UCARE Polymer JR-30M: MW = 2,000,000 g/mol, CD = 1.3 meq/g, supplier: Dow Chemical

[11] Carbopol Aqua SF-1 at 30% active, supplier: Lubrizol

[12] DSM Nutritional Products (Ayrshire GB)

[13] Roche Vitamins Inc.

[14] Croda

[15] Sodium Benzoate Dense NF/FCC, supplier: Emerald Performance Materials

[16] Dissolvine 220-S at 84% active, supplier: Akzo Nobel

[17] Kathon CG at 1.5% active, supplier: Rohm & Haas

[18] Salicylic Acid, USP, supplier: Novacyl

[19] Citric Acid Anhydrous, supplier: Archer Daniels Midland; level adjustable to achieve target pH

[20] Sodium Citrate Dihydrate, supplier: ADM Company; level adjustable to achieve target pH

[21] Sodium Chloride, supplier: Morton; level adjustable to achieve target viscosity Key (1) Sodium Laureth Sulfate from P&G Chemicals (2) Sodium Lauryl Sulfate from Stepan Company (3) Sodium Cocoyl isethionate from Innospec (4) Sodium Lauroyl methyl isethionate from Innospec (5) Sodium Lauroyl Sarcosinate from Croda (6) Lauramidopropyl Betaine less than 1% NaCl from Solvay (7) Lauramidopropyl Betaine less than 1% NaCl from Evonik (8) Cocamide MEA from Stepan (9) Acrylate copolymer from BASF

(10) Trihydrostearin from Elementis

(11) Glycol Distearate from Goldschmidt Chemical Company

(12) Octopirox, supplier: Clariant

(13) Roche Vitamins Inc.

(14) DSM Nutritional Products (Ayrshire GB)

(15) Polyquaternium-10 from Dow

(16) Guar Hyrdroxypropyltrimonium Chloride (LMW) ~500k MW, 0.7 CD from Ashland

(17) Guar Hyrdroxypropyltrimonium Chloride BF17 (HMW) ~800k MW, 1.5 CD from Ashland

(18) Polyquaternium-76 from Solvay

(19) Perfume from Givuadan

(20) Dimethicone DC 1872 from Dow

(21) Dimethicone DC330M from Dow

(22) Citric acid from Acher Daniels Midland

(23) Hydrochloric acid from Mallinckrodt Baker Inc.

(24) Methylchloroisothiazolinone/Methylisothiazolinone (Kathon) from Rohm and Haas

(25) Sodium Salicylate from Novacyl

(26) Sodium Chloride from Morton

(27) Sodium Benzoate from Kalama Chemical

(28) Water and Minors (QS to 100%) from Misty Mountain Spring water

| | Examples | |
|---|---|---|
| | 10 Active wt %) | 11 Active wt %) |
| Water | Q.S. | Q.S. |
| Alcohol 100% (Ethanol) | 50 | 50 |
| Acrylates/C10-30 alkyl acrylate crosspolymer *1 | 0.35 | |
| FlexiThix ™ *2 | | 2.6% |
| Bis-PEG/PPG-16/16 PEG/PPG 16/16 Dimethicone *3 | 0.7 | |
| Panthenol *4 | 0.15 | 0.2 |
| Niacinamide *5 | 2.5 | 2.5 |
| Caffeine *6 | 0.75 | |
| Piroctone Olamine*7 | | 0.45 |
| Climbazole *8 | 0.50 | |
| Butylene Glycol *9 | 1.0 | |
| Benzyl Alcohol *10 | 0.5 | |
| Ginger Root Extract*11 | | 0.1 |
| Tetrahydroxypropyl Ethylenediamine *12 | 0.05 | |

Key
*1 as in Carbopol Ultrez 21 available from Lubrizol
*2 as in FlexiThix ™ from Ashland Chemical.
*3 as in Abil Care 85 from Evonik
*4 as in Dexapaanthenol USP from Roche Vitamins
*5 as in Niancinamide USP from Roche Vitamins
*6 as in Caffeine USP from BASF
*7as Octopirox, supplier: Clariant
*8 as in Crinipan AD from Symrise
*9 as in Cosmetic Quality 1,3-Butylene Glycol from Oxea Corporation
*10 as in Benzyl Alcohol from Polarome International
*11as in Croda
*12as in Neutrol Te from BASF

| Components | 12 | 13 | 14 | 15 | 16 |
|---|---|---|---|---|---|
| Niacinamide *1 | 0.005 | 1.8 | — | 0.8 | 0.005 |
| Panthenol *2 | 0.005 | 0.005 | 0.03 | 0.2 | 0.2 |
| Piroctone Olamine*3 | 0.5 | 0.8 | — | 0.8 | 0.5 |
| Behenyl trimethyl ammonium chloride | — | — | — | 2.5 | 0.9 |
| Behenyl trimethyl ammonium methosulfate | 2.6 | 2.6 | 2.97 | — | |
| Dicetyl dimethyl ammonium chloride | — | 0.35 | — | — | |
| Cetyl alcohol | 1.0 | 1.0 | 1.18 | 1.0 | 1.0 |
| Stearyl alcohol | 2.4 | 2.4 | 2.95 | 2.3 | 2.3 |
| Aminosilicone *4 | 0.5 | 0.5 | 1.5 | 0.5 | 0.5 |
| Benzyl alcohol | | | 0.4 | | |
| Preservatives | 0.9 | 0.9 | 0.9 | 0.9 | 0.9 |
| Perfume | 0.5 | 0.5 | 0.5 | 0.5 | 0.5 |
| Histidine | | | 0.03 | | |
| Ginger Root Extract*5 | | | 0.1 | | |
| Panthenyl ethyl ether | — | — | — | 0.03 | |
| Deionized Water | | q.s. to 100% | | | |

Definitions of Components
*1 Roche Vitamins Inc.
*2 DSM Nutritional Products (Ayrshire GB)
*3Octopirox from Clairiant
*4 Aminosilicone: Terminal aminosilicone which is available from GE having a viscosity of about 10,000 mPa · s, and having following formula: $(R_1)_aG_{3-a}$—Si—(—$OSiG_2)_n$—O—$SiG_{3-a}(R_1)_a$ wherein G is methyl; *a* is an integer of 1; *n* is a number from 400 to about 600; $R_1$ is a monovalent radical conforming to the general formula $C_qH_{2q}L$, wherein q is an integer of 3 and L is —$NH_2$.
*5Croda Product Form The hair care compositions of the present invention may be presented in typical hair care formulations. They may be in the form of solutions,]dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, pre-wash product, co-wash product, and personal cleansing products, and treatment products; and any other form that may be applied to hair.

Additional Examples/Combinations

A. A personal care composition comprising:
a) a hydroxy pyridone;
b) niacinamide; and
c) panthenol;
wherein when the hydroxy pyridone is at about 0.8%, there is a synergistic antioxidant activity when niacinamide is from about 0.005% to about 0.1% and panthenol is from about 0.005% to about 0.2%.

B. A personal care composition according to Paragraph A, comprising:
a) a hydroxy pyridone;
b) niacinamide; and
c) panthenol;
wherein when the hydroxy pyridone is at 0.5%, there is a synergistic antioxidant activity when:
i) panthenol is at 0.005% and niacinamide is from about 0.005% to about 1%; or
ii) panthenol is from about 0.01% to about 0.05% and niacinamide is from about 0.005% to about 0.1%; or
iii) panthenol is at 0.1% and niacinamide is from about 0.005% to about 0.05%; or
iv) panthenol is at 0.005% and niacinamide is from about 0.005% to about 0.01%.

C. A personal care composition according to Paragraph A-B, comprising:
a) a hydroxy pyridone;
b) niacinamide; and
c) panthenol;
wherein when the hydroxy pyridone is from about 0.5% to about 0.8%, there is a synergistic antioxidant activity when:
i) panthenol is from about 0.005% to about 0.05% and niacinamide is from about 0.005% to about 0.1%; or
ii) panthenol is at 0.1% and niacinamide is from about 0.005% to about 0.05%; or panthenol is at 0.2% and niacinamide is from about 0.005% to about 0.01%.

D. A personal care composition according to Paragraph A-C, wherein the personal care composition is selected from group consisting of a shampoo, conditioner, leave-on, tonic and mixtures thereof.

E. A personal care composition according to Paragraph A-D, wherein the hydroxy pyridone is from about 0.1% to about 10%, by weight of the composition.

F. A personal care composition according to Paragraph A-E, wherein the hydroxy pyridone is from about 0.3% to about 3%, by weight of the composition.

G. A personal care composition according to Paragraph A-F, wherein the hydroxy pyridone is from about 0.5% to about 2%, by weight of the composition.

H. A personal care composition according to Paragraph A-G, wherein the hydroxy pyridone is piroctone olamine.

I. A personal care composition according to Paragraph A-H, wherein the niacinamide material is from about 0.001% to about 5%, by weight of the composition.

J. A personal care composition according to Paragraph A-I, wherein the niacinamide material is from about 0.005% to about 3%, by weight of the composition.

K. A personal care composition according to Paragraph A-J, wherein the panthenol is from about 0.001% to about 3%, by weight of the composition.

L. A personal care composition according to Paragraph A-K, wherein wherein the panthenol is from about 0.005% to about 1%, by weight of the composition.

M. A method of using a composition according to Paragraph A-L, comprising:

a) a hydroxy pyridone;

b) niacinamide c) panthenol;

wherein when the hydroxy pyridone is at about 0.8%, there is a synergistic antioxidant activity when niacinamide is from about 0.005% to about 0.1% and panthenol is from about 0.005% to about 0.2%.

N. A method of using a composition according to Paragraph A-M, comprising:

a) a hydroxy pyridone;

b) niacinamide;

c) panthenol;

wherein when the hydroxy pyridone is at 0.5%, there is a synergistic antioxidant activity when:

i) panthenol is at 0.005% and niacinamide is from about 0.005% to about 1%; or ii) panthenol is from about 0.01% to about 0.05% and niacinamide is from about 0.005% to about 0.1%; or iii) panthenol is at 0.1% and niacinamide is from about 0.005% to about 0.05%; or iv) panthenol is at 0.005% and niacinamide is from about 0.005% to about 0.01%.

O. A method of using a composition according to Paragraph A-N, comprising:

a) a hydroxy pyridone;

b) niacinamide;

c) panthenol;

wherein when the hydroxy pyridone is from about 05% to about 0.8%, there is a synergistic antioxidant activity when:

i) panthenol is from about 0.005% to about 0.05% and niacinamide is from about 0.005% to about 0.1%; or ii) panthenol is at 0.1% and niacinamide is from about 0.005% to about 0.05%; or iii) panthenol is at 0.2% and niacinamide is from about 0.005% to about 0.01%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm.”

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:

a) piroctone olamine;

b) niacinamide; and c) panthenol;

wherein piroctone olamine is at about 0.8%, niacinamide is from about 0.005% to about 0.1% and panthenol is from about 0.005% to about 0.2%, wherein there is a synergistic antioxidant activity, said synergistic antioxidant activity demonstrating an observed ATP level for the composition that is higher than the calculated sum of individual observed ATP levels for each component, as measured by a Peroxide-Induced Keratinocyte Stress assay.

2. A personal care composition comprising:

a) piroctone olamine;

b) niacinamide; and c) panthenol;

wherein piroctone olamine is at 0.5%,:

i) panthenol is at 0.005% and niacinamide is from about 0.005% to about 1%; or ii) panthenol is from about 0.01% to about 0.05% and niacinamide is from about 0.005% to about 0.1%; or iii) panthenol is at 0.1% and niacinamide is from about 0.005% to about 0.05%; or panthenol is at 0.005% and niacinamide is from about 0.005% to about 0.01%, wherein there is a synergistic antioxidant activity, said synergistic antioxidant activity demonstrating an observed ATP level for the composition that is higher than the calculated sum of individual observed ATP levels for each component, as measured by a Peroxide-Induced Keratinocyte Stress assay.

3. A personal care composition comprising:

a) piroctone olamine;

b) niacinamide; and c) panthenol;

wherein piroctone olamine is from about 0.5% to about 0.8%,:

i) panthenol is from about 0.005% to about 0.05% and niacinamide is from about 0.005% to about 0.1%; or ii) panthenol is at 0.1% and niacinamide is from about 0.005% to about 0.05%; or iii) panthenol is at 0.2% and niacinamide is from about 0.005% to about 0.01%, wherein there is a synergistic antioxidant activity, said synergistic antioxidant activity demonstrating an observed ATP level for the composition that is higher than the calculated sum of individual observed ATP levels for each component, as measured by a Peroxide-Induced Keratinocyte Stress assay.

4. A personal care composition according to claim 1 wherein the personal care composition is selected from group consisting of a shampoo, conditioner, leave-on, tonic and mixtures thereof.

* * * * *